United States Patent [19]
Gordon

[11] 4,397,647
[45] Aug. 9, 1983

[54] CATHETER STABILIZATION FITTING HAVING A SNAP-OVER COVER

[75] Inventor: Marvin Gordon, East Windsor, N.J.

[73] Assignee: Whitman Medical Corporation, Clark, N.J.

[21] Appl. No.: 353,928

[22] Filed: Mar. 2, 1982

Related U.S. Application Data

[63] Continuation-in-part of Ser. No. 168,721, Jul. 14, 1980, abandoned, which is a continuation-in-part of Ser. No. 5,032, Jan. 19, 1979, Pat. No. 4,224,937, which is a continuation-in-part of Ser. No. 905,399, May 12, 1978, abandoned.

[51] Int. Cl.³ .............................................. A61M 5/00
[52] U.S. Cl. .......................... 604/180; 128/DIG. 26
[58] Field of Search ..................... 128/214, 133, 214.4, 128/215, 347, 348, 349, DIG. 6, DIG. 26; 604/180, 174, 178

[56] References Cited
U.S. PATENT DOCUMENTS

| | | | |
|---|---|---|---|
| 2,525,398 | 10/1950 | Collins ................................ | 128/215 |
| 2,707,953 | 5/1955 | Ryan ............................... | 128/214 R |
| 3,059,645 | 10/1962 | Hasbrouck et al. ........ | 128/DIG. 26 |
| 3,167,072 | 1/1965 | Stone et al. .......................... | 128/348 |
| 3,834,380 | 9/1974 | Boyd .......................... | 128/DIG. 26 |
| 3,856,020 | 12/1974 | Kovac .................................. | 128/347 |
| 4,020,835 | 5/1977 | Nordstrom et al. ............ | 128/214.4 |
| 4,082,094 | 4/1978 | Dailey ................................. | 128/214 |
| 4,129,128 | 12/1978 | McFarlane ......................... | 128/133 |
| 4,161,171 | 7/1979 | Fuchs ............................... | 128/214.4 |

*Primary Examiner*—Stephen C. Pellegrino
*Attorney, Agent, or Firm*—Holman & Stern

[57] ABSTRACT

A disposable stabilizing fitting for a catheter tube includes a laminar base member having an adhesive coated underside and a tube-retaining cradle. A snap-over cover engages the catheter tube in the cradle. Specifically, gripping members in the cradle are non-aligned with one or more gripping members in the cover such that the gripping members engage the catheter tube by bending the tube slightly without restricting flow. In one preferred embodiment, the cradle is subdivided into two longitudinal sections having respective covers which hinge in opposite directions and are latchable in a plurality of positions corresponding to various catheter tube diameters.

19 Claims, 9 Drawing Figures

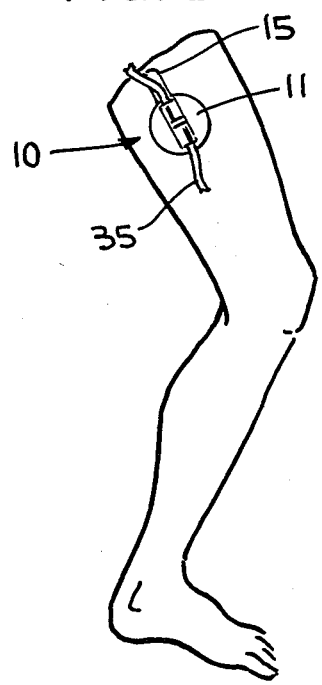
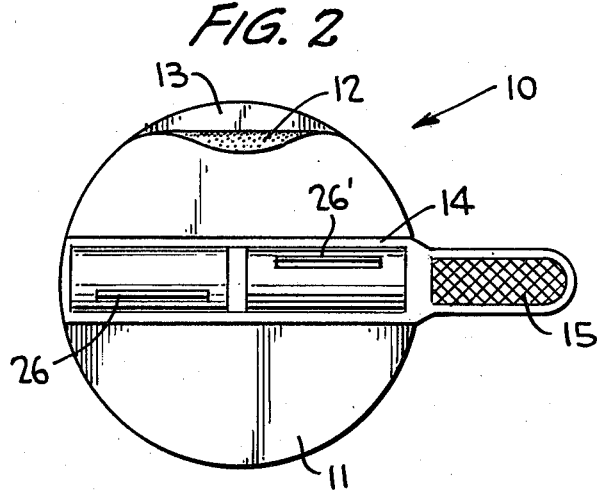
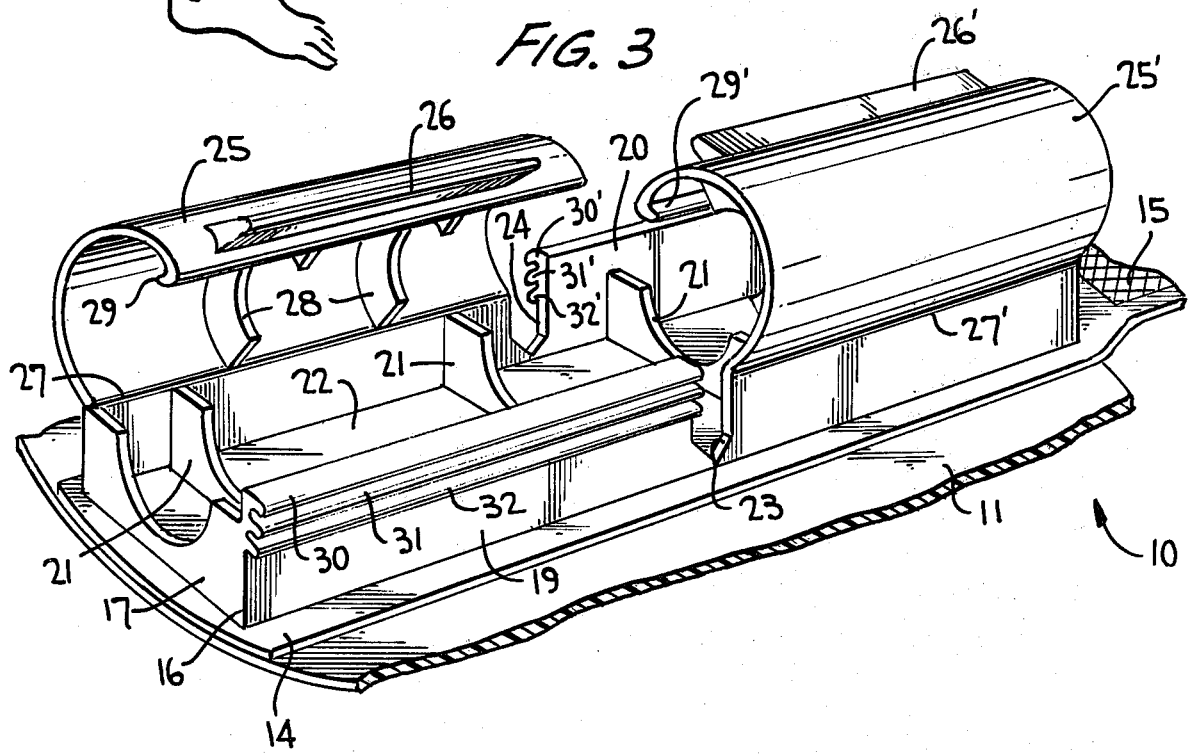

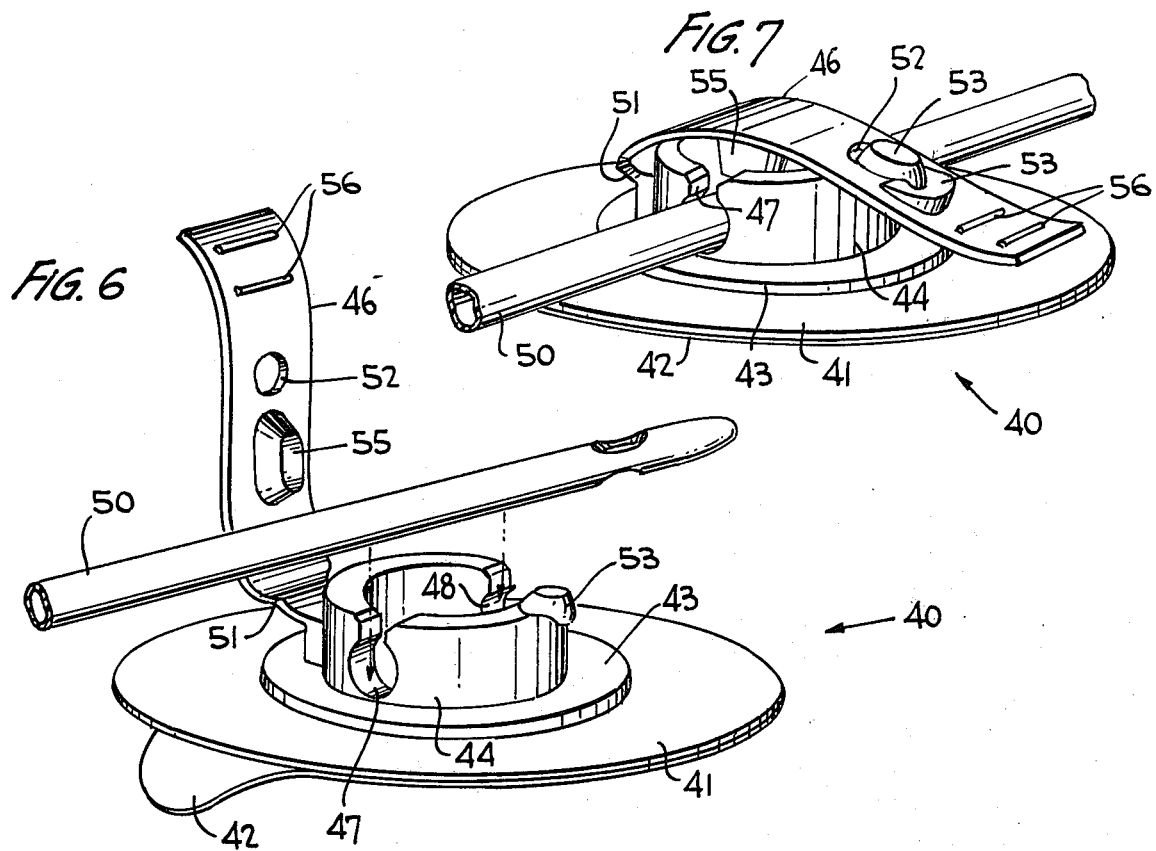
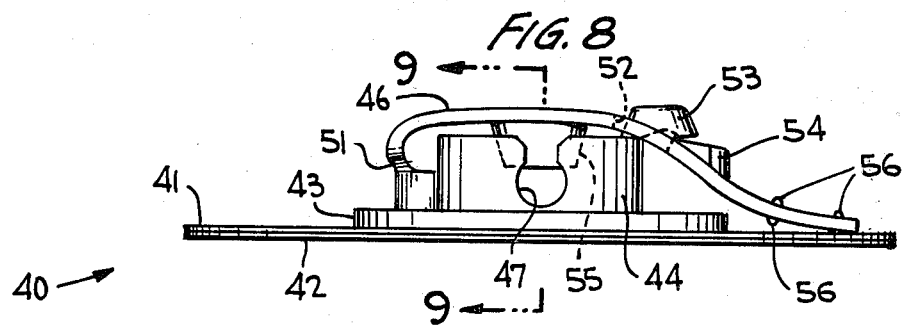
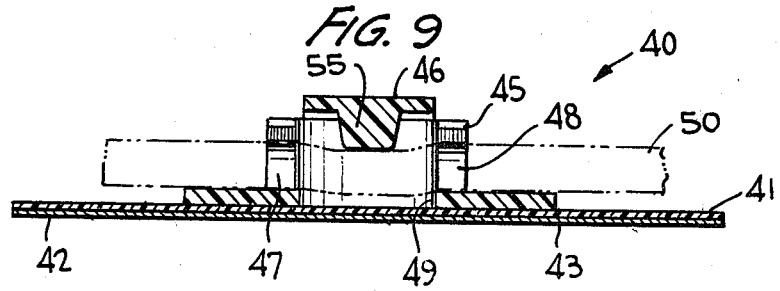

CATHETER STABILIZATION FITTING HAVING A SNAP-OVER COVER

CROSS-REFERENCE TO RELATED APPLICATIONS

This application is a Continuation-in-Part of my copending U.S. patent application Ser. No. 168,721, filed July 14, 1980 now abandoned, and bearing the title "CATHETER STABILIZATION FITTING HAVING A SNAP-OVER COVER", which application is a Continuation-in-Part of my copending U.S. patent application Ser. No. 5,032 filed Jan. 19, 1979 now U.S. Pat. No. 4,224,937, and bearing the title "STABILIZING FITTING FOR AN INTRAVENOUS CATHETER", which application is a Continuation-in-Part application of my U.S. patent application Ser. No. 905,399, filed May 12, 1978 now abandoned. May aforesaid U.S. Patent Application Ser. No. 5,032, is expressly incorporated herein by reference.

TECHNICAL FIELD

The present invention relates to devices for positionally stabilizing a catheter on the body of a patient. Although described herein specifically in terms of a "fully-indwelling" catheter, the present invention encompasses stabilization of intravenous type catheters in the manner described in reference to FIGS. 16 and 17 of my aforementioned U.S. patent application Ser. No. 5,032 incorporated herein by reference.

BACKGROUND OF THE INVENTION

Urethral catheter stabilizing devices are required to perform two (2) primary functions. First, the device must hold the catheter tube positionally stabilized relative to the device itself. Second, the device itself must be held positionally stabilized relative to the body of the patient. Prior art urethral catheter holding devices generally fail to satisfactorily perform one or both of these functions. For example, some devices require conventional adhesive tape to be secured to the patient's skin; such tape, as a general rule, does not hold in place for any considerable period of time and is often time-consuming and bothersome to employ. Other devices utilize stretch rubber strips with VELCRO fastening devices wherein the strips encircle the patient's thigh; these are unsatisfactory because, in order to prevent the device from slipping along the thigh, the strips must be wrapped so tightly as to constrict blood circulation. Other devices hold the tube by means of some snap-fit engagement; such devices are subject to displacement of the catheter tube from the device and to movements which inadvertently remove the tube from the snap-fit. Still other devices require that the tube be tied, taped, or similarly engaged to the device; such arrangements tend to restrict the flow through the catheter tube. Finally, there are other devices which require special configurations of catheter tubes to engage the tube properly; such custom tubing requirements are clearly undesirable since it will not be useful for the majority of commercially available catheters.

SUMMARY OF THE INVENTION

It is therefore a primary object of the present invention to provide a stabilizing device for indwelling catheters which can be stabilized with respect to the patient's body, and which can stabilize a catheter tube with respect to the device so that the attendant disadvantages described above for prior art devices are eliminated. Particularly, it is an object of the present invention to provide a disposable and inexpensive catheter stabilizing device using principles that are adaptable to both indwelling and intravenous type catheters. It is another object of the present invention to provide a catheter-stabilizing device which provides complete security against unwanted longitudinal movement of the catheter in spite of extensive movements by the patient. It is a further object of the present invention to provide a catheter-stabilizing device which is capable of performing the desired functions with catheter tubes having a variety of different diameters. Still another object of the present invention is to provide a catheter-stabilizing device with all of the attendant advantages described herein and which is waterproof so as to permit a patient to shower without the fear of dislodging the catheter.

In accordance with the present invention, a disposable catheter-stabilizing holder includes a base member having an adhesive coating on its lower surface, which coating is covered by a peel-away covering until the device is ready for use. A tube-retaining cradle is secured to the surface of the laminar base member which is not covered by adhesive. The cradle includes a body portion with one or more upstanding gripping members having aligned recesses for supporting an elongated catheter tube. A snap-over cover hinges to one side wall of the cradle and is arranged to engage a latch member on the opposite side wall so as to hold the catheter tube in the cradle and prevent both longitudinal and transverse catheter tube movement. Specifically, the cover is provided with at least one downwardly-extending gripping member which is longitudinally misaligned with the upstanding gripping members so as to slightly deform the catheter tube, when the cover is closed, without restricting flow through the tube, and thereby providing secure longitudinal stabilization of the catheter tube.

In one embodiment, the upstanding members are arcuately recessed ribs and the downwardly-extending members are similarly recessed ribs. In another embodiment, the upstanding members are side walls joining at common recesses at their opposite ends whereas the downwardly-extending member is a projection from the cover into the space between the recesses.

The latch member and cover preferably have a plurality of settings in order that the device may accommodate different diameter tubes; however, the non-aligned gripping members permit secure stabilization of catheter tubes having sizes which do not necessarily correspond to the specific positions of the latch and cover. It is also a preferred, although not necessary, part of the present invention to provide two (2) longitudinally-arranged sections wherein each section has its own snap-over cover and offset gripping member arrangements and wherein the covers pivot in opposite rotational directions. This opposite cover arrangement provides reliability, not only by means of redundancy, but also by means of the fact that any movement which might inadvertently tend to open a cover hinged in one direction while not necessarily open the cover hinged in the opposite direction. A tap grip is provided, extending from the laminar base member, on which no adhesive backing is utilized, so that the device can be readily held between the thumb and the forefinger of one hand while stripping the adhesive backing from the bottom of the device and applying the adhesive-coated surface of the base member to the patient's skin.

BRIEF DESCRIPTION OF THE DRAWINGS

The above and still further objects, features and advantages of the present invention will become apparent upon consideration of the following detailed description of specific embodiments thereof, especially when taken in conjunction with the accompanying drawings, wherein:

FIG. 1 is a view is perspective showing a catheter stabilizing device of the present invention secure to the inner thigh of a patient;

FIG. 2 is a top view in plan of the catheter-stabilizing device of the present invention;

FIG. 3 is a view in perspective of the catheter-stabilizing device of FIG. 1 showing the covers for the device in their open condition;

FIG. 6 is a view in perspective showing another catheter-stabilizing device in accordance with the present invention with the cover of the stabilizing device open and a cathether tube positioned prior to insertion into the stabilizing device cradle;

FIG. 7 is a view similar to FIG. 6 showing the catheter tube in the cradle and the stabilizing device closed;

FIG. 8 is a plan view in elevation showing the catheter-stabilizing device of FIGS. 6 and 7 in its closed position; and FIG. 9 is a view in section taken along lines 9—9 of FIG. 8, with a catheter tube shown in phantom lines to illustrate the gripping characteristic of the stabilizing device.

DESCRIPTION OF THE PREFERRED EMBODIMENT

Figure 4:
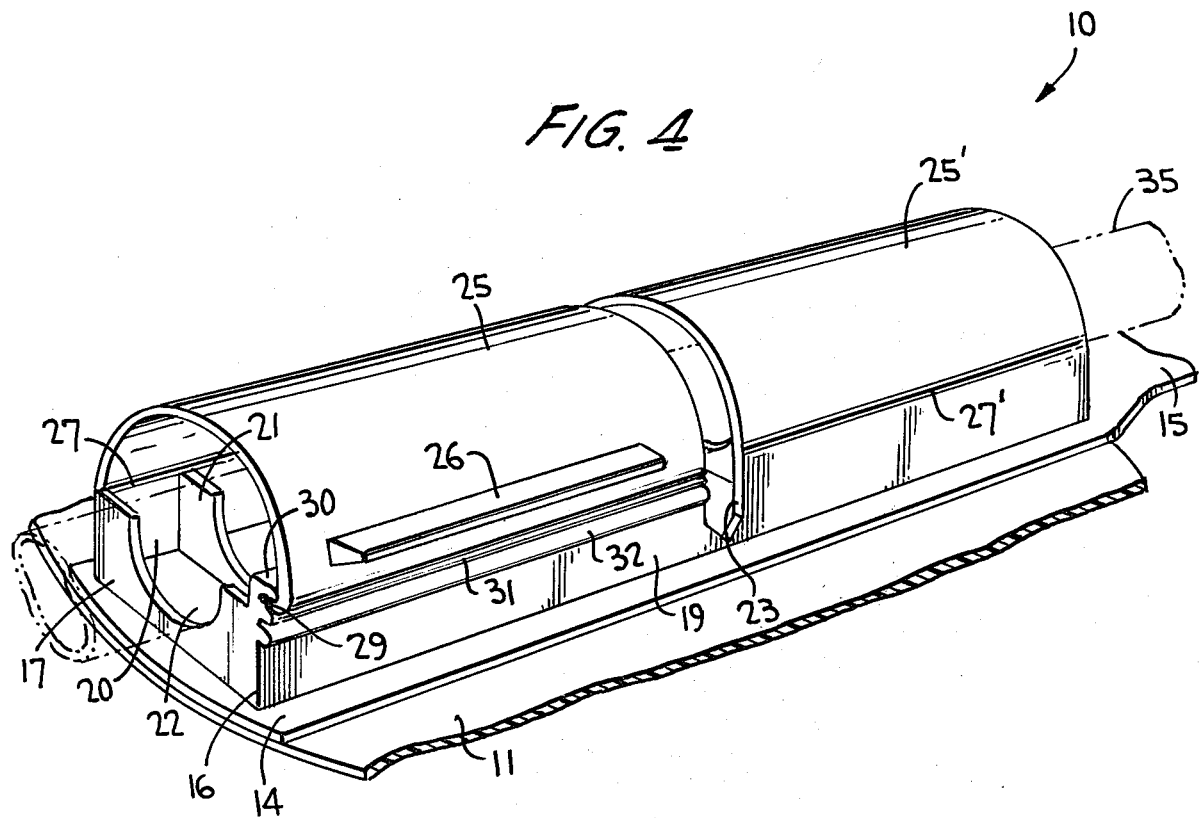
FIG. 4 is a view in perspective of the catheter-stabilizing device of FIG. 3 showing the covers of the device in their closed condition.

Referring more specifically to the drawings, a catheter-stabilizer 10 includes a laminar base member 11 which is shown in the form of a circle but which may take any configuration appropriate to the area of the body of a patient to which the stabilizer is to be secured. Base member 11 may be a thin sheet of plastic material, such as polyethylene tape, or it may be a somewhat thicker but still very much flexible plastic foam material. In either case, the underside of base member 11 is coated with a pressure-sensitive adhesive material 12 which, prior to deployment of the stabilizer, is covered with a protective peel-away or strippable covering sheet 13. A support member 14 made of flexible plastic material such as polyvinylchloride or polyethylene, is heat-sealed or otherwise secured to the top surface of base member 11. Support member 14 is in the form of a strip which extends at least partially across the base member 11 and is integral with a tab grip 15 extending beyond the periphery of base member 11. Tab grip 15 is devoid of adhesive material and thereby may serve as means for holding the device when the backing 13 is removed and during the deployment of stabilizer 10.

A cradle 16, which is preferably molded integrally with support member 14, includes a front wall 17, a rear wall 18 and side walls 19 and 20. A bottom wall 22, which may be one and the same with support member 14, is surrounded by walls 17, 18, 19 and 20. Gripping members in the form of upstanding ribs 21, comprise wall members extending parallel to the front wall 17 and the rear wall 18 and longitudinally spaced within cradle 16. There are four (4) such ribs 21 employed in the embodiment described herein, however, it is to be understood that the number of such ribs may vary within the scope of the present invention. The front wall 17, rear wall 18, and the ribs 21 are provided with arcuate recesses which are longitudinally aligned.

Cradle 16 is sub-divided longitudinally into two (2) sections by means of respective notches 23 and 24, defined in side walls 19 and 20. The notches extend substantially through the entire height of the side walls and terminate in a generally V-configuration, the base of which defines a transverse line across the cradle along which the cradle may be bent. The forward end of cradle 16 includes a cover 25 hinged at the top of side wall 20 and extending along the entire length of the front section of the cradle. Cover 25 has a generally C-chaped or other arcuate transverse cross-section whereby it domes upwardly from the cradle. Although the hinging mechanism between cover 25 and the top of side wall 20 may be a multipart hinge arrangement, the hinging mechanism is preferably a thinned portion 27 of the integrally molded cradle which, as is conventional, permits the integral cover to flexibly pivot about the top of side wall 20. The outer surface of cover 25 includes a longitudinally-extending handle portion 26 disposed proximate the end of the cover removed from hinged region 27. Handle 26, as the name implies, permits the user to grasp the handle to control the position of the cover 25.

An interior surface of cover 25 is provided with gripping members or downwardly-extending ribs 28 which are arcuately recessed upwardly with a configuration similar but oppositely directed to recesses in ribs 21. Importantly, ribs 28 are longitudinally offset from ribs 21 and, in the particular embodiment illustrated in FIGS. 1-6, ribs 28 are disposed between the ribs 21 of the forward section of the cradle. The side of cover 25 removed from hinged portion 27 includes an inward projection 29 extending longitudinally along the entire length of cover 25.

The top of side wall 19 in the forward half of cradle 16 includes a latch mechanism suitable for engagement with projection 29 and cover 25. Specifically, the latch mechanism includes three (3) vertically spaced longitudinally extending ribs 30, 31 and 32, the uppermost rib 30 being disposed above the normal edge of the side wall 19 whereas the lowermost rib 32 is disposed below the nominal top of side wall 19. Ribs 30, 31 and 32 are positioned to provide resilient engagement with projection 29 and cover 25 so as to provide different selective closure positions for the cover.

The rearward half of cradle 16 is provided with a cover 25'. Cover 25' is identical to cover 25 and all of its parts are designated by primed reference numerals corresponding to the reference numerals utilized to designate the parts of cover 25. The only difference between the two covers is that cover 25' is hinged atop side wall 19 and latches with the ribs disposed along the side wall 20. Therefore, the two covers pivot in opposite directions.

Figure 5:
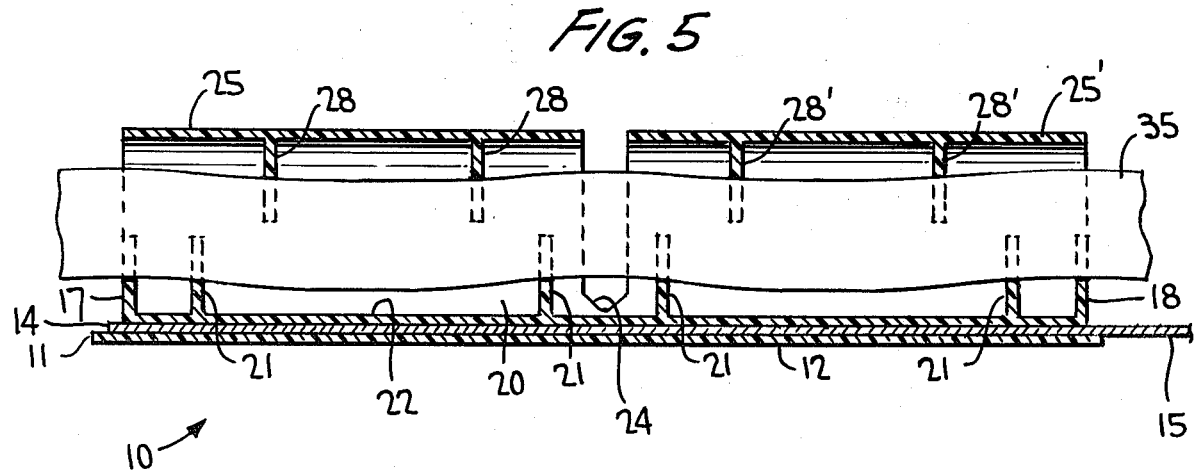
FIG. 5 is a view in section showing the catheter-stabilizing device of FIG. 1 engaging a catheter tube.

In use, the stabilizer can be secured to the catheter tube either before or after the catheter has been inserted into the patient. Likewise, the catheter tube can be secured in the stabilizer before or after the stabilizer has been secured to the patient's skin. In either case, the tube is secured to the stabilizer 10 by opening covers 25 and 25' and disposing the tube 35 along the longitudinally aligned recesses in ribs 21. When the tube is so positioned, the covers 25 and 25' are pivoted closed so that projections 29, 29' engage the appropriate ribs 30, 30', or 31, 31', or 32, 32', depending upon the diameter of tube 35. Preferably, the three (3) latching positions correspond to engagement of tubing diameters of 16 mm, 18 mm, and 20 mm. Of course, the stabilizer can be designed for other diameter tubing. It should be noted that when the covers 25, 25' are closed, the vertical spacing between the recessed portions of ribs 21 and 28 is slightly less than the diameter of the engaged tube 35. Since ribs 21 and 28 are offset longitudinally, this reduced spacing forces a slight crimping (as illustrated in FIG. 5) of the tube 35, thereby providing a firm engagement of the tube with the stabilizer. Importantly, this crimping is small enough to provide the desired firm engagement without restricting the flow through the tube. This feature permits the stabilizer to engage tubing having a diameter which is somewhat smaller than the three sizes for which the stabilizer is primarily designed. This feature of serving other diameter tubing, however, is secondary to the fact that the crimping feature is primarily intended to provide a firm grip against longitudinal displacement of the tubing within the stabilizer.

In applying the stabilizer to the patient's skin, the backing 13 is removed from the adhesive-coated underside of base member 11 with one hand as the other hand grips hand grip 15. The exposed adhesive coating 12 is then pressed against the desired location of the skin, again while holding hand grip 15 to facilitate positioning.

The release paper, or backing paper 13 may be slit along a transverse line parallel to and immediately below the line defined between the bottom-most portions of notches 23 and 24. This facilitates backing removal prior to use of the stabilizer since the stabilizer can be flexed along notches 23 and 24 causing the release paper to separate along the cover, thereby permitting the user to easily peel off the backing.

Although the embodiment of FIGS. 1-6 utilizes two oppositely pivoted covers 25, 25', a positive gripping arrangement provided by non-aligned recessed ribs 21, 28 in just one half of the stabilizer unit is sufficient to provide the necessary gripping of the catheter tube to prevent a longitudinal slipping. The value of the two longitudinal halves of the stabilizer resides in the fact that the covers 25, 25' are pivoted in opposite directions. This feature prevents dislodgement of the catheter tube 35 from the stabilizer in the event that one cover should open. Suppose, for example, that a patient moves and impacts an an object in such a manner that cover 25 is inadvertently opened, such an impact could likely occur on the side of the stabilizer at which hing 27 is located (i.e., side wall 20) such that cover 25 is pushed in the direction of side wall 19 and projection 29 is slipped out of engagement with one of the ribs 30, 31, 32. Impact along the hinged side of cover 25, however, corresponds to impact along the latching side of cover 25'. Such impact on the latching side of cover 25' tends to force projection 29 into further engagement with one of the ribs 30', 31', 32'. Likewise, transverse movement of the tube 35 which would tend to inadvertently open one of the covers, would tend to further engage the latching of the other cover. Thus, the position of the two covers 25, 25' is more than merely a redundant feature.

Support member 14 can be eliminated entirely in which case the cradle 16 is heat-sealed directly to base member 11; under such circumstances tab member 15 would extend to cradle 16. In any event, the entire cradle 16 can readily be injection-molded in one piece; likewise, the combination of support member 14 and the cradle 16 can be injection-molded in one piece. The stabilizer is therefore inexpensive to manufacture, and can be sold as a readily disposable unit after a single use. Notwithstanding this low cost, the device still retains the advantage of providing the necessary retention of the tube in a secure positioning of the device on the patient's body while being simple and comfortable to use.

Another catheter-stabilizer embodiment of the present invention is illustrated in FIGS. 6-9 and is generally designated by the reference numeral 40. Stabilizer 40 includes a laminar base member 41 which is shown in the form of a circle, but which may take any configuration appropriate to the area of the body of a patient to which the stabilizer is to be secured. Base member 41 may be a thin sheet of plastic material, such as polyethylene tape, or it may be a somewhat thicker but still very much flexible plastic foam material. In either case, the underside of base member 41 is coated with a pressure-sensitive adhesive material which, prior to deployment of the stabilizer, is covered with a protective or peel-away or strippable covering sheet 42. An integrally formed rubber or other elastomer structure is secured to the top side of base member 41 and includes a generally circular (although the circular configuration is by no means limiting) base portion 43, a pair of upstanding arcuate side walls 44, 45 and a snap-over cover member 46. The upstanding side walls 44 and 45 constitute opposed portions of a circle which is concentrically disposed within the circular base portion 43. Opposed ends of the side walls 44, 45 terminate in respective aligned recesses 47, 48 which extend substantially to base portion 43 from diametrically opposed locations of the circle formed by the side walls. Each recess 47, 48 includes an upper neck portion which is relatively narrow and which terminates at its bottom in a generally circular portion having its opposite end approximately tangential with base portion 43. The neck portion of recesses 47 and 48 is narrower than the diameter of the catheter tube 50 which is to be secured in place by the stabilizer 40. The bottom circular portion of the recesses 47, 48, on the other hand, have substantially the same diameter as the catheter tube 50 so as to permit the catheter tube 50 to be slidable longitudinally within the recesses 47, 48. In this regard, the catheter tube may be inserted from above through the neck portions of recesses 47 and 48, by flexing the two (2) side walls 44 and 45 away from one another and forcing the catheter tube into the circular portions of the recesses. Alternatively, the catheter tube may be slid longitudinally in place through the two (2) circular portions of the recesses 47 and 48. It should be noted, however, that for some applications it may be desirable that the diameter of the circular portions of recesses 47 and 48 be slightly smaller than the outside diameter of catheter tube 50 so as to firmly engage the catheter tube in place when the tube is properly inserted into the stabilizer.

The snap-over cover 46 is in the form of a strap secured to the outer surface of side wall 45 at a location substantially 90° displaced from each of recesses 47 and 48. The strap 46 includes a relatively thin portion 51 near its proximal end which serves as a hinge to provide the cover 46 to be folded over the space above the two (2) side walls 44 and 45 in the manner illustrated in FIGS. 7, 8 and 9. A through hole 52 is defined in the strap or cover 46 in a position to mate with a projecting latch 53 formed integrally with the top edge of side wall 44 at a location spaced 90° from each of recesses 47 and 48. The latch member 53 projects radially outward somewhat from side wall 44 and is configured to permit the latching hole 52 of the strap 46 to be stretched over projection 53 so that the projection extends through the hole and latches the cover in place. The latched condition is illustrated in FIGS. 7 and 8. The top side of strap 46 includes a raised member 54 disposed on the side of latching hole 52 remote from hing 51. Member 54 includes a top surface which is oblique relative to the top surface of strap 46 so as to slope downward toward hole 52. When the cover is in its closed position, the underside of projection 53 rests on the sloped surface of projection 54. This engagement between the underside of projection 53 and the sloped surface of projection 54 facilitates opening of the cover when the distal end of strap 46 is pulled upwardly from the position illustrated in FIGS. 7 and 8. Specifically, when the distal end of strap 46 is pulled upwardly, the underside of projection 53 slides along the slope surface of projection 54 while the opposite end of the hole 52 engages the presented surface of projection 53 which is likewise sloped. The annular boundary of hole 52 thus slides along the sloped projection 53 while the underside of the projection 53 slides along the surface of projection 54 to facilitate removal of the projection from the hole.

The underside of strap 46 is provided with a gripping projection 55 which is positioned lengthwise along strap 46 so as to project downwardly between side walls 44 and 45 when the strap is latched closed. The gripping projection extends sufficiently far down into the space between the side walls 44 and 45 to engage and slightly crimp the catheter tube 50 (as best illustrated in FIG. 9), forcing the catheter tube slightly downward into the central opening 49 at the center of the annular base portion 43. More specifically, the side walls 44 and 45 have their inner surfaces disposed to extend vertically upward from the periphery of the central opening 49 in the base portion 43. This circular space below the bottom of recesses 47 and 48 permits the projection 55 to force the catheter tube 50 below the bottom of recesses 47 and 48 so that a transverse gripping effect is achieved.

The distal end of the strap may be provided with raised ridges 56 on one or both sides thereof to facilitate gripping of the strap for purposes of latching and unlatching.

It should once again be emphasized that the base portion 43, side walls 44, 45, strap 46, projection 55 and projection 53 are formed integrally as one (1) piece of rubber or other elastomeric material. The stabilizer 40 is therefore simply and inexpensively manufactured by conventional molding processes.

In the preferred embodiment, the projection 55 takes the form of an oval in transverse cross-section with decreasing dimensions so that the tube engaging surface is of smaller area than the area of intersection with strap 46. This smaller contact area permits greater pressure to be exerted on the catheter tube 50.

As noted above, latching projection 53 has sloped sides to facilitate latching and unlatching by forcing the hole 52 resiliently along the sloped sides.

Although the embodiments described herein relate primarily to use with urethral catheters, it should be evident to one of ordinary skill in the art that the same concept can be utilized to stabilize hyperalimentation, nasalgastric tubes, nephrostomy tubes, cystostomy tubes, chest drainage tubes, etc. Moreover, the same concept described herein relates to intravenous catheter stabilization in the manner described in my aforementioned U.S. patent application Ser. No. 5,032. The different between stabilizing indwelling catheter tubes and intravenous catheter tubes relates to the fact that the stabilization of the intravenous catheter tube makes use of the varied configuration of a catheter hub so that a particular locating means is utilized for longitudinally positioning the catheter hub in the stabilizer. For the indwelling catheter, the tube has no hub but is merely a flexible tubing which can be positioned anywhere along its length within the stabilization device. In that context, the claimed tube is held longitudinally in place by means of the off-set ribs 21, 28 and their longitudinally aligned recesses which slightly crimp the tube.

The instant invention is not to be limited to the embodiment of the invention as herein described, for various modifications can be made by a person skilled in the art without detracting from the true spirit and scope of the invention as defined in the appended claims.

What is claimed is:

1. A stabilizing fitting for securing a catheter to a patient's skin comprising a laminar base member having an upper surface and a lower surface, pressure-sensitive adhesive means on at least a part of said lower surface of said base member, a catheter tube-retaining cradle secured to said upper surface of said base member, said cradle having a forward end, a rearward end, and resilient substantially parallel side walls, said side walls being spaced to receive a catheter tube placed longitudinally in said cradle, a tab grip extending beyond the periphery of said base member, a snap-over cover hinged to the upper edge of one of said side walls and including means for positively contacting said catheter tube and urging the catheter tube toward said lower surface, and latching engagement means on the other of said side walls for holding the cover in place in a flexibly removable engagement over a tube disposed in said cradle.

2. A stabilizing fitting for securing a catheter to a patient's skin comprising a laminar base member having an upper surface and a lower surface, pressure-sensitive adhesive means on at least a part of said lower surface of said base member, a catheter tube-retaining cradle secured to said upper surface of said base member, said cradle having a forward end, a rearward end, and resilient substantially parallel side walls, said side walls being spaced to receive a catheter tube placed longitudinally in said cradle, a tab grip extending beyond the periphery of said base member, a snap-over cover hinged to the upper edge of one of said side walls, and latching engagement means on the other of said side walls for holding the cover in place in a flexibly removable engagement over a tube disposed in said cradle; and further including at least one upstanding rib member in said cradle disposed parallel to said forward end, said upstanding rib member being arcuately recessed to support a catheter tube therein;

a further rib member secured to said cover and depending downwardly toward said cradle, said further rib member being upwardly recessed to receive a catheter tube;

wherein said upstanding rib member and said further rib member are longitudinally spaced from one another such that, with said cover closed, the recesses in said rib members engage a catheter tube in said cradle at different locations.

3. The stabilizer fitting according to claim 2, wherein the recesses in said rib members are configured to crimp a catheter tube in said cradle when said cover is closed to thereby positively prevent longitudinal movement of such catheter tube.

4. The stabilizer fitting according to claims 1 or 3, wherein said cradle is divided into two longitudinally aligned sections spaced by transversely aligned first and second notches defined in respective side walls of said cradle, said snap-over cover being coextensive with the first of said cradle sections, said stabilizer fitting further comprising a second snap-over cover hinged to the upper edge of said other of said side walls and latching means secured on said one of said side walls for providing a resilient engagement holding said further cover in place over said catheter hub fitting, whereby said covers are arranged to hinge in opposite directions over a catheter tube disposed in said cradle.

5. A stabilizing fitting for securing a catheter to a patient's skin comprising a laminar base member having an upper surface and a lower surface, pressure-sensitive adhesive means on at least a part of said lower surface of said base member, a catheter tube-retaining cradle secured to said upper surface of said base member, said cradle having a forward end, a rearward end, and resilient substantially parallel side walls, said side walls being spaced to receive a catheter tube placed longitudinally in said cradle, a tab grip extending beyond the periphery of said base member, a snap-over cover hinged to the upper edge of one of said side walls, and latching engagement means on the other of said side walls for holding the cover in place in a flexible removable engagement over a tube disposed in said cradle; and further comprising means for positively engaging a catheter tube, said means comprising:
an arcuate recess defined in said forward end of said cradle;
at least one upstanding rib member disposed in said cradle longitudinally spaced and parallel to said forward end, said rib member having an arcuate recess defined therein in longitudinal alignment with the recess in said forward end;
a further rib member depending from said other in longitudinally spaced relationship to said forward end and said first-mentioned rib member, said further rib member having an arcuate recess which is aligned with the arcuate recesses of said forward end and said first-mentioned rib member when said cover is closed, said arcuate recesses and said rib member being sized to slightly bend a catheter tube disposed longitudinally between the recesses.

6. The stabilizing fitting according to claim 5, wherein said cover includes a longitudinally extending inward projection and said latching engagement means includes a plurality of longitudinally extending spaced ribs on said other side wall arranged to be resiliently engaged by said projection.

7. A stabilizing fitting for securing a catheter to a patient's skin comprising a laminar base member having an upper surface and a lower surface, pressure-sensitive adhesive means on at least a part of said lower surface of said base member, a catheter tube-retaining cradle secured to said upper surface of said base member, said cradle having a forward end, a rearward end, and resilient substantially parallel side walls, said side walls being spaced to receive a catheter tube placed longitudinally in said cradle, a tab grip extending beyond the periphery of said base member, a snap-over cover hinged to the upper edge of one of said side walls, and latching engagement means on the other of said side walls for holding the cover in place in a flexibly removable engagement over a tube disposed in said cradle; wherein said cradle and said cover comprise an integral injection-molded unit.

8. A stabilizing fitting for a flexible catheter tube comprising:
a flexible base member having a pressure-sensitive adhesive-coated underside, said base member being sufficiently flexible to conform to the contours of a patient's skin;
a cradle member secured to said base member, said cradle member having first and second longitudinally aligned sections for receiving respective longitudinal portions of said catheter tube, said cradle member having first and second side walls;
a first cover member coextensive with said first longitudinal section of said cradle, and hinged to said first side wall;
first latching means for securing said first cover member to said second side wall of said first cradle section;
a second member hinged to said second side wall; and
second latching means for resiliently engaging said second member to said first side wall.

9. The stabilizer fitting according to claim 8, further comprising means for positively gripping said catheter tube between said cradle and said first and second cover members.

10. The stabilizer fitting according to claim 9, further characterized by means of a notch defined in said first and second side walls between said first and second longitudinal sections of said cradle to permit bending of said cradle at said notch.

11. A stabilizing fitting for securing a catheter to a patient's skin comprising a laminar base member having an upper surface and a lower surface, pressure-sensitive adhesive means on at least a part of said lower surface of said base member, a catheter tube-retaining cradle secured to said upper surface of said base member, said cradle having a forward end, a rearward end, and resilient substantially parallel side walls, said side walls being spaced to receive a catheter tube placed longitudinally in said cradle, a tab grip extending beyond the periphery of said base member, a snap-over cover hinged to the upper edge of one of said side walls, and latching engagement means on the other of said side walls for holding the cover in place in a flexibly removable engagement over a tube disposed in said cradle, wherein the cover includes a longitudinally extending inward projection and said latching engagement means includes a plurality of longitudinally-extending spaced ribs on said other side wall arranged to be resiliently engaged by said projection.

12. A stabilizing fitting for securing a catheter to a patient's skin comprising a base having an upper surface and a lower surface, pressure-sensitive adhesive means secured to at least a part of said lower surface of said base, a catheter tube-retaining cradle secured to said upper surface of said base member, said cradle having a forward end, a rearward end, and resilient side walls, means for receiving a catheter tube placed longitudinally in said cradle between said side walls, a snap-over cover hinged to one of said side walls to move between opened and closed positions and including means for positively contacting said catheter tube in said closed position to urge the catheter tube toward said base, and latching engagement means on the other of said side walls for holding the cover in place in a flexibly removable engagement over a catheter tube disposed in said cradle, wherein said cover includes a latching through hole and wherein said latching engagement means comprises a latching projection secured to said other side walls, said through hole being positioned to align with and resiliently fit over said latching projection when said cover is in said closed position.

13. A stabilizing fitting for securing a catheter to a patient's skin comprising a base having an upper surface and a lower surface, pressure-sensitive adhesive means secured to at least a part of said lower surface of said base, a catheter tube-retaining cradle secured to said upper surface of said base member, said cradle having a forward end, a rearward end, and resilient side walls, means for receiving a catheter tube placed longitudinally in said cradle between said side walls, a snap-over cover hinged to one of said side walls to move between opened and closed positions and including means for positively contacting said catheter tube in said closed position to urge the catheter tube toward said base, latching engagement means on the other of said side walls for holding the cover in place in a flexibly removable engagement over a catheter tube disposed in said cradle;

and further including:

at least one upstanding rib member in said cradle disposed parallel to said forward end, said upstanding rib member being arcuately recessed to support a catheter tube therein;

a further rib member secured to said cover and depending downwardly toward said cradle, said further rib member being upwardly recessed to receive a catheter tube;

wherein said upstanding rib member and said further rib member are longitudinally spaced from one another such that, when the cover is closed, the recesses in said rib members engage a catheter tube in said cradle at different longitudinal locations; and wherein the recesses in said rib members are configured to crimp a catheter tube in said cradle when said cover is closed to thereby positively prevent longitudinal movement of said catheter tube.

14. A stabilizing fitting for securing a catheter to a patient's skin comprising a base having an upper surface and a lower surface, pressure-sensitive adhesive means secured to at least a part of said lower surface of said base, a catheter tube-retaining cradle secured to said upper surface of said base member, said cradle having a forward end, a rearward end, and resilient side walls, means for receiving a catheter tube placed longitudinally in said cradle between said side walls, a snap-over cover hinged to one of said side walls to move between opened and closed positions and including means for positively contacting said catheter tube in said closed position to urge the catheter tube toward said base, and latching engagement means on the other of said side walls for holding the cover in place in a flexibly removable engagement over a catheter tube disposed in said cradle;

wherein said base is an annular member having a generally circular hole at its center, wherein said side walls are arcuate upstanding walls disposed about the periphery of said circular hole, and wherein said means for receiving comprises a pair of diametrically opposed recesses defined between facing ends of said arcuate side walls.

15. The stabilizing fitting according to claim 14, wherein said recesses each have a top neck portion which is narrower than the diameter of said catheter tube and a bottom circular portion having a diameter substantially equal to that of said catheter tube.

16. The stabilizer fitting according to claim 15, wherein said cover includes a latching through hole and wherein said latching engagement means comprises a latching projection secured to said other side wall, said through hole being positioned to align with and resiliently fit over said latching projection when said cover is in said closed position.

17. The stabilizer fitting according to claim 12, wherein said cover, said base, said side walls, and said latching projection are part of an integrally-formed elastomeric structure.

18. The stabilizer fitting according to claim 12, wherein said cover is a strap-like member having a top side and a bottom side, and wherein said strap-like member includes a sloped surface portion positioned adjacent said through hole to contact said latching projection when said through hole is fitted over said latching projection, said sloped surface providing a camming action when the latched cover is lifted so as to facilitate disengagement of said latching projection and said through hole.

19. The stabilizer fitting according to claim 18, wherein said positively contacting means comprises a latching projection from said bottom side of said strap-like member, and latching projection having a perimeter at its distal end which is smaller than its perimeter at its proximal end.

* * * * *